(12) United States Patent
Bliss

(10) Patent No.: US 9,018,239 B2
(45) Date of Patent: Apr. 28, 2015

(54) TREATMENT OF EDIBLE CROPS

(76) Inventors: William Bliss, Pakenham (AU); Sandra Bliss, legal representative, Pakenham (AU)

( * ) Notice: Subject to any disclaimer, the term of this patent is extended or adjusted under 35 U.S.C. 154(b) by 179 days.

(21) Appl. No.: 13/465,083

(22) Filed: May 7, 2012

(65) Prior Publication Data

US 2012/0277276 A1 Nov. 1, 2012

Related U.S. Application Data

(63) Continuation-in-part of application No. 12/301,079, filed as application No. PCT/AU2007/000694 on May 18, 2007, now abandoned.

(30) Foreign Application Priority Data

May 18, 2006 (AU) ................................ 2006902660

(51) Int. Cl.
*A01N 43/50* (2006.01)
*A01N 59/00* (2006.01)
*A01N 25/02* (2006.01)

(52) U.S. Cl.
CPC ................. *A01N 59/00* (2013.01); *A01N 25/02* (2013.01)

(58) Field of Classification Search
None
See application file for complete search history.

(56) References Cited

U.S. PATENT DOCUMENTS

2009/0016990 A1 * 1/2009 Alberte et al. ............... 424/85.5

FOREIGN PATENT DOCUMENTS

JP 2002275008 A * 9/2002

OTHER PUBLICATIONS

Brown et al., Brit J industry Med 23:302 (1966).*
NJ Hazardous Substance Fact Sheet—Diacetone Alcohol. [downloaded Jun. 13, 2014 from the website http://nj.gov/health/eoh/rtkweb/documents/fs/0606.pdf].*
OSHA Guidelines—diacetone alcohol, 1988. [downloaded Jun. 13, 2014 from the website http://www.cdc.gov/niosh/docs/81-123/pdfs/0178.pdf].*

* cited by examiner

*Primary Examiner* — Robert A Wax
*Assistant Examiner* — Thor Nielsen
(74) *Attorney, Agent, or Firm* — Edwin D. Schindler

(57) ABSTRACT

In the growing of crops for consumption, a method for the removal of pathogens includes the addition to irrigation water for the crops of an anti-pathogen composition and supplying the anti-pathogen composition to the crops prior to harvest while normal irrigation is effected. The anti-pathogen composition is based on halogens, such as chlorine, bromine and iodine, or mixtures of halogens or halogens combined with other organic radicals including cyanurate, hydantoin, peroxide and chlorine dioxide. BCDMH and TICA are preferred anti-pathogen components of the anti-pathogen composition and may be added to a carrier concentrate and measured and dosed into the irrigation water.

7 Claims, No Drawings

TREATMENT OF EDIBLE CROPS

CROSS-REFERENCE TO RELATED PATENT APPLICATION

This is a continuation-in-part of application Ser. No. 12/301,079, filed Nov. 17, 2008, now abandoned, which represents the U.S. National Phase application of P.C.T. Application No. PCT/AU 2007/000694, filed May 18, 2007, the entire disclosure of which shall be deemed to be incorporated by reference herein.

BACKGROUND OF THE INVENTION

1. Technical Field of the Invention

The present invention relates to the treatment of edible crops and, in particular, to pre-harvest treatment of such crops.

2. Description of the Prior Art

A very large proportion of edible crops are irrigated by overhead sprays. Crops grown in proximity of urban areas may utilize potable mains water for this use. However, due to the expansion of urban population traditional vegetable growing areas are being displaced to areas where irrigation supplies are dependant on dams or rivers. Surface water as above is contaminated by livestock, poultry and misdirected sewage effluent. This contamination results in a growth of undesirable human pathogens in the water supply. The trend to recycle drainage water and run off from the growing area to conserve water, results in increasing the level of plant pathogens in the irrigation supply. Total Plate Count (TPC) of this water will give a typical figure of $10^6$ of Colony Forming Units CFU/ml indicating a high level of contamination. In addition, faecal contamination will show coliform counts of $10^1$-$10^3$ ml.

In developed countries, the general requirements for ready-to-eat foods is for a TPC of $10^3$/gm or less and nil coliforms. Quite obviously, the contaminated irrigation water is not helping achieve the food safety requirement.

A further issue in terms of food safety is pesticide residues. As most vegetable crops require generous watering this increases the humidity adjacent the crop and, in turn, results in prime conditions for fungal diseases.

Many of these diseases develop very rapidly and a whole crop can be wiped out in a few days.

While a pesticide spray would control the fungal problem it may leave a residue on the crop at harvest.

The residue, at the time of harvest, cannot exceed the Maximum Residue Level (MRL). To avoid exceeding the MRL a time interval is determined between spraying the pesticide and harvest. This time is called the Withholding Period.

Consequently, if a fungal problem occurs close to harvest it may not be possible to use any pesticide on the crop because of the withholding period.

SUMMARY OF THE INVENTION

It is an object of the present invention is to provide means whereby edible crops can be treated for the removal of human and plant pathogens from their surfaces prior to harvest with a lesser withholding period than has presently been the case so treatment can occur much later than is the case using pesticides.

The present invention includes in the growing of crops for consumption, the removal of pathogens by the addition to irrigation water for the crops of an anti-pathogen compound and supplying this to the crop prior to harvest while normal irrigation is effected.

It is preferred that the anti-pathogen material be based on halogens, such as, for example, chlorine, bromine and iodine or mixtures of halogens or halogens combined with other organic radicals including cyanurate, hydantoin, peroxide and chlorine dioxide. In addition it is required that the active ingredient be measured and dosed with a sensing probe such as ORP.

It is preferred that the anti-pathogen material be bromochlorodimethyl-hydantoin ("BCDMH") or trichloro-isocyanuric acid ("TICA"), and it is also preferred to make a concentrate of this product with a solvent, which concentrate can be metered into the irrigation water. The preferred solvents are non-toxic, biodegradable, inert solvents, which are water-soluble and have a molecular weight in the range of approximately 100 to 130. In one particularly preferred embodiment of the invention, di-acetone alcohol or a non-toxic solvent having a molecular weight in the range from approximately 100 to about 130 can be used, along with a silica drier, if required.

DETAILED DESCRIPTION OF THE PREFERRED EMBODIMENTS

In order that the present invention may be more readily understood, a particularly preferred embodiment of the present invention shall now be described:

It is often necessary to remove human and plant pathogens from the surface of edible crops and in many applications the crops, after harvest, go through a treatment process which may include dipping or spraying with an anti-pathogen material, such as, for example, BCDMH (bromochlorodimethyl-hydantoin) or TICA (trichloro-iso-cyanuric acid). This means that the crops, after harvest, and still carrying substantial quantities of pathogens, are transported to a treatment site, with the possibility that cross-contamination from the untreated crops can occur.

BCDMH is currently registered in Australia and New Zealand for the control of plant and human pathogens on fruit and vegetables by washing, dipping or spraying as a post-harvest treatment.

It is proposed to treat the crop before harvest with these products and this will reduce the quantity of pathogens which are carried with the newly harvested material, which would normally still pass through a post-harvest treatment although, in some cases, this may not be necessary.

The withholding period in this use pattern is 15 minutes, when BCDMH is used at 5-22.5 ppm as chlorine. Current fieldwork indicates that a few "troublesome" crops may require higher rates of 50-100 ppm as chlorine, which could extend the withholding period to 60 minutes.

These periods are very much shorter than possible from normal pesticides and thus crops can be treated much closer to harvest than has previously been the case.

As described, the pre-harvest irrigation water containing BCDMH would reduce the pathogen level on all wetted surfaces of the crop.

The formulation described in this invention allows the product to be used in water or in mineral oil as for misting bananas. Other vegetable oils (e.g., canola oil) are used with pesticides. Another development is synthetic oils or materials, such as polysilicones. The formulation is designed for addition to such systems.

Provided is a base concentrate material and, in one particular arrangement, this may comprise:

| | |
|---|---|
| di-acetone alcohol | 1 liter |
| BCDMH | 350 grams |
| silica drier | 10 grams |

While in this particular formulation di-acetone alcohol is used, the solvent that may be used may be any other solvent having a molecular weight in the range of from about 100 to about 130, such as glycol alcohols or glycol ethers, with the basic requirement being that the solvent, or any residue which it leaves, is non-toxic. The preferred solvents are those which are non-toxic, biodegradable, inert solvents, which are water soluble and have a molecular weight in the range of from approximately 100 to about 130.

The BCDMH can be replaced by TICA or other suitable anti-pathogen compound.

The concentrate may, if required, be diluted with a compatible mineral, plant or animal oil prior to use, or the concentrate is miscible with water in all proportions. In an emulsion this will permit the disinfectant to be present in either an oil phase, water phase or both.

The concentrate may be mixed with the irrigation water used for a number of different types of irrigation. For example, it is particularly useful for treatment when applied through overhead sprinkler or spray irrigation systems or other forms of spray units. This tends to bring the material into contact with the crop from above, so there is good coverage of the crop.

When the product is to be used to control soil borne plant pathogens, it can readily be applied by flood, furrow, overhead or trickle irrigation systems.

Where the present invention is to be used on the surface of crops, it can also be applied by land-based spray or misting equipment or be delivered by rotary or fixed wing aircraft.

While the concept of the invention appears to be deceptively simple, it provides a completely new direction of human and plant pathogen control.

While only several embodiments of the present invention have been shown and described, it will be obvious to those skilled in the art that many modifications may be made to the present invention without departing from the spirit and scope thereof.

What is claimed is:

1. A method for removing pathogens from crops being grown and intended for human consumption, comprising the steps of:

providing an anti-pathogenic composition to irrigation water for crops being grown and intended for human consumption, the anti-pathogenic composition comprising a silica drier and a halogen-based component comprising bromochlorodimethyl-hydantoin, wherein the amount ranges from 5 to 100 ppm as chlorine, the anti-pathogenic composition being in a solution having a non-toxic solvent with a high molecular weight;

metering the addition of the anti-pathogenic composition when in the solution comprising the non-toxic solvent into the irrigation water, wherein the anti-pathogenic composition comprising bromochlorodimethyl-hydantoin ranges from 5 to 100 ppm as chlorine; and, applying the irrigation water to the crops prior to harvesting thereof.

2. The method for removing pathogens from crops being grown and intended for human consumption according to claim 1, wherein the halogen-based component includes a halogen compound having chlorine with bromochloro-dimethyl-hydantoin being included in an amount ranging from 5 to 22.5 ppm as chlorine, and with a withholding period of 15 minutes.

3. The method for removing pathogens from crops being grown and intended for human consumption according to claim 1, wherein the halogen-based component includes a halogen compound having chlorine with bromochloro-dimethyl-hydantoin being included in an amount ranging from 50 to 100 ppm as chlorine, and with a withholding period of 60 minutes.

4. The method for removing pathogens from crops being grown and intended for human consumption according to claim 1, wherein the solvent for said anti-pathogen composition is di-acetone alcohol.

5. The method for removing pathogens from crops being grown and intended for human consumption according to claim 1, wherein the solvent for said anti-pathogen composition is a non-toxic, biodegradable, water-soluble solvent.

6. The method for removing pathogens from crops being grown and intended for human consumption according to claim 1, wherein the solvent for said anti-pathogen composition is a non-toxic glycol alcohol.

7. The method for removing pathogens from crops being grown and intended for human consumption according to claim 1, wherein the solvent for said anti-pathogen composition is a non-toxic glycol ether.

\* \* \* \* \*